US00PP28699P3

(12) United States Plant Patent
Wood

(10) Patent No.: US PP28,699 P3
(45) Date of Patent: Nov. 28, 2017

(54) ***HYDRANGEA* PLANT NAMED 'SMHPCW'**

(50) Latin Name: ***Hydrangea* hybrid**
Varietal Denomination: SMHPCW

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 24 days.

(21) Appl. No.: 14/998,609

(22) Filed: Jan. 20, 2016

(65) Prior Publication Data

US 2017/0208717 P1 Jul. 20, 2017

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Cassandra Bright

(57) ABSTRACT

A new and distinct *Hydrangea* cultivar named 'SMHPCW' is disclosed, characterized by early flowering with flowers that turn pink to deep pink mid to late summer, strong stems and compact growth habit. The new variety is a *Hydrangea,* normally produced as an ornamental plant for containers or gardens.

3 Drawing Sheets

Latin name of the genus and species: *Hydrangea* hybrid. Variety denomination: 'SMHPCW'.

BACKGROUND OF THE INVENTION

The new *Hydrangea* cultivar is a product of a planned breeding program conducted by the inventor, Timothy D. Wood, in Grand Haven, Mich. The objective of the breeding program was to produce new *Hydrangea.* The open pollination resulting in this new variety was made during July of 2008.

The seed parent is the unpatented commercial variety *Hydrangea paniculata* 'SMHPRZEP' The pollen parent is unknown, both in variety name and species, as it was an open pollination breeding program. The new variety was identified as a potentially interesting selection July of 2010, at a greenhouse in Grand Haven, Mich.

Asexual reproduction of the new cultivar 'SMHPCW' by softwood cuttings was first performed during the July of 2013, at commercial greenhouse in Grand Haven, Mich. Subsequent propagation has shown that the unique features of this cultivar are stable and reproduced true to type in 2 successive generations.

SUMMARY OF THE INVENTION

The cultivar 'SMHPCW' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMHPCW' These characteristics in combination distinguish 'SMHPCW' as a new and distinct *Hydrangea* cultivar:

1. Compact plant.
2. Early flowering.
3. Strong stems.

4. Flowers emerge white, then turn pink to deep pink mid to late Summer.

PARENT COMPARISON

Plants of the new cultivar 'SMHPCW' are similar to plants of the seed parent, *Hydrangea paniulata* 'SMHPRZEP' in most horticultural characteristics, however, plants of the new cultivar 'SMHPCW' differ in the following:

1. Earlier to bloom.
2. Flowers age to magenta pink. The seed parents ages to a lighter pink.
3. Branches grow upright and outward. The seed parent branches only upright.

Pollen parent unknown as this is a product of open pollination.

COMMERCIAL COMPARISON

'SMHPCW' can be compared to the patented commercial variety *Hydrangea* 'SMNHPPINKA', U.S. Plant Pat. No. 26,977. These varieties are similar in most horticultural characteristics; however 'SMHPCW' differs in the following:

1. Earlier blooming.
2. Flowers age to magenta pink. The comparator ages to a lighter pink.

BRIEF DESCRIPTION OF THE PHOTOGRAPHS

The accompanying photograph in FIG. 1 illustrates in full color a typical plant of 'SMHPCW' grown outdoors, in Grand Haven, Mich., USA, in the ground. Flowers on the plant are both the younger white flowers and older pink flowers.

Figure 1:
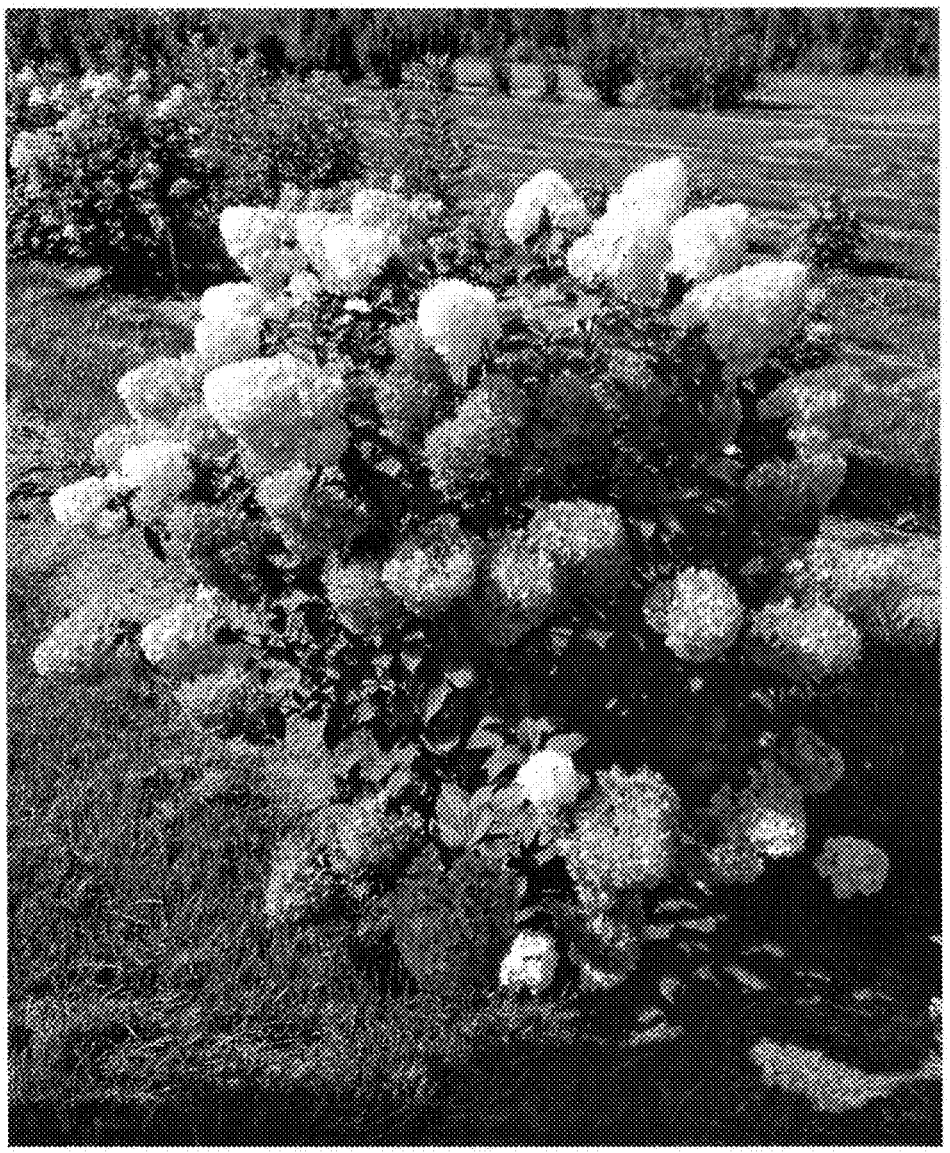
Figure 2:
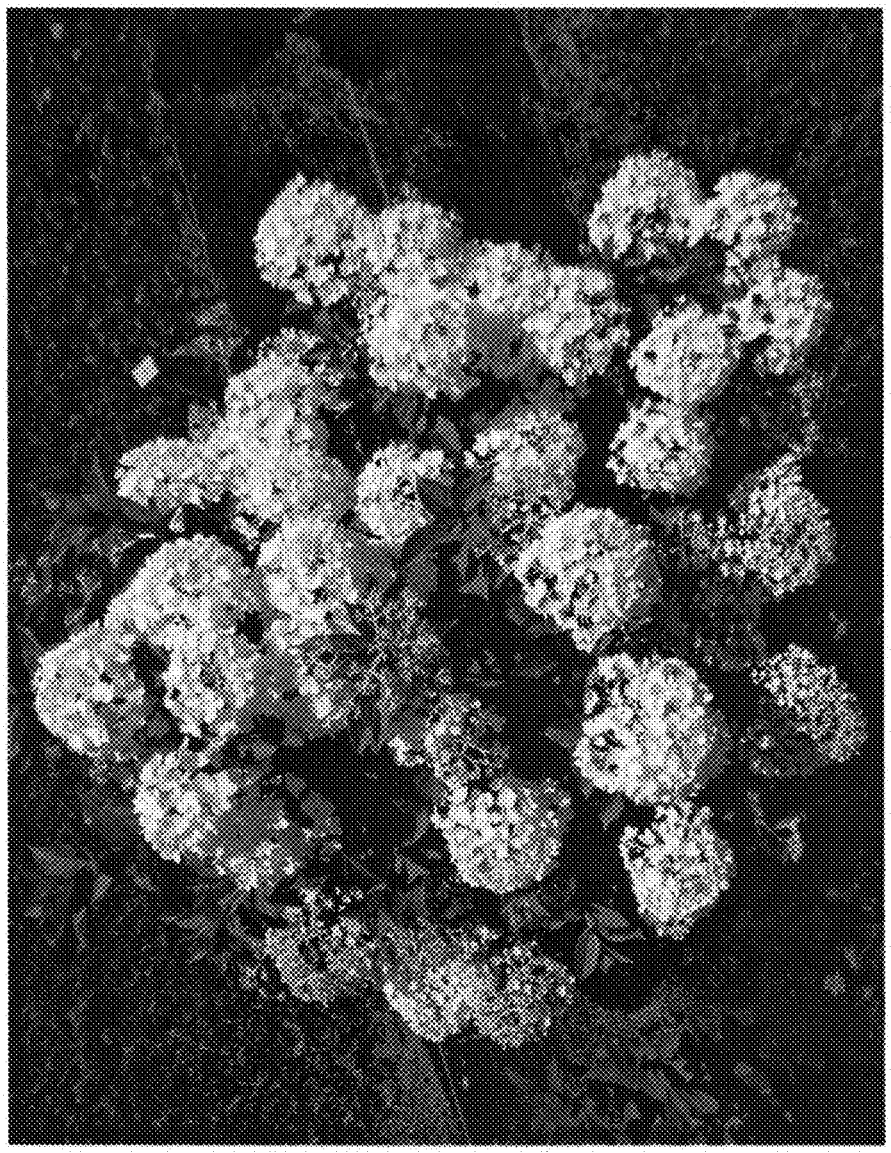
FIG. 2 illustrates in full color typical young flowers, which are white.
Figure 3:
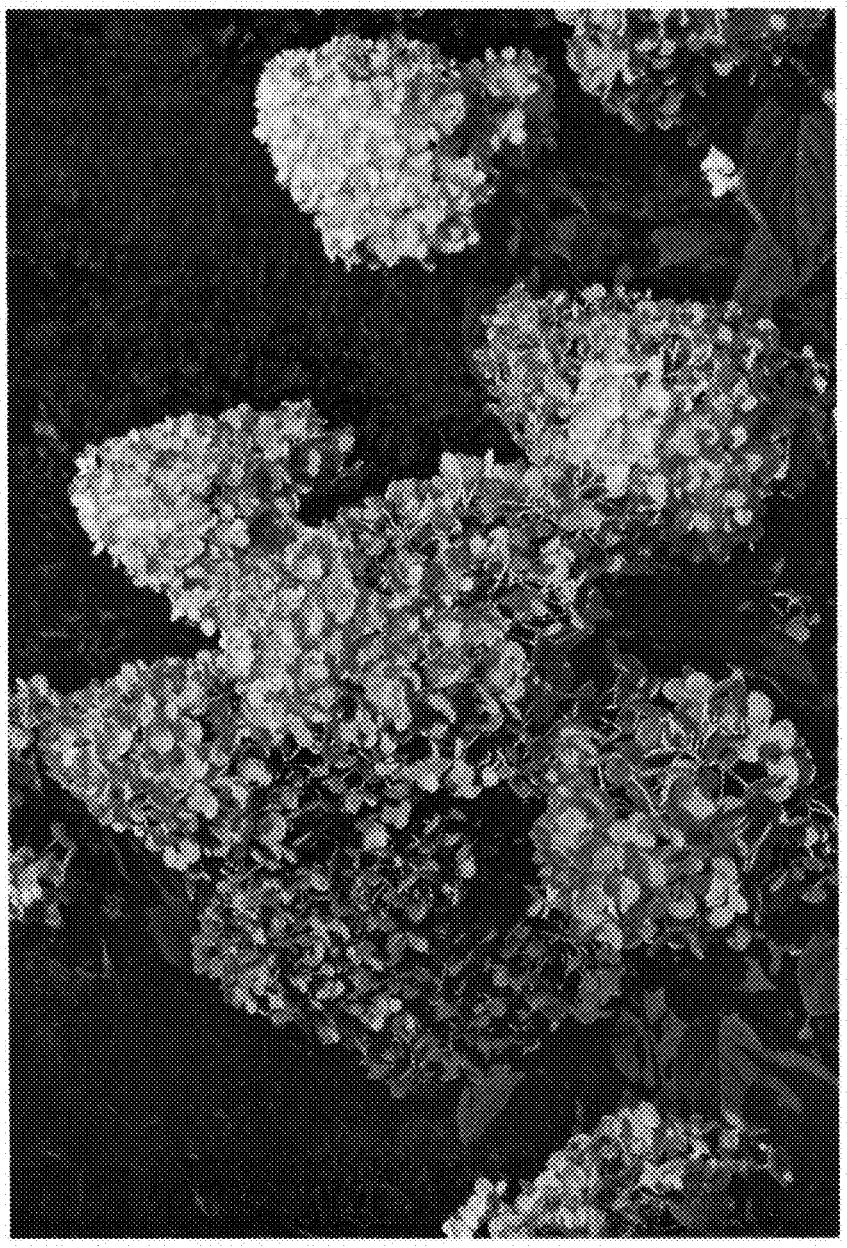
FIG. 3 illustrates the most mature flowers, colored dark pink. Age of the plants photographed is approximately 2-3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 2015 Royal Horticultural Society Colour Chart except where general terms of ordinary dictionary significance are used. The following observations and measurements describe 'SMHPCW' plants grown in a double layered poly greenhouse, in Grand Haven, Mich., USA. The growing temperature ranged from approximately 18° C. to 27° C. daytime and 5° to 10° C. at night. Measurements and numerical values represent averages of typical plant types. Measurements were taken during July to August of 2015. Botanical classification: *Hydrangea* hybrid 'SMHPCW'.

PROPAGATION

Time to initiate roots: Approximately 18 days at approximately 24° C.

Time to produce a rooted young plants: Approximately 90 days at approximately 24° C.

Root description: Medium thickness, moderate root branching and density, both fibrous and fleshy. Color is white, not accurately identified with The R.H.S. chart.

Propagation method: Softwood cuttings.

PLANT

Age of plant described: 2-3 years.

Pot size: 2 gallon.

Growth habit: Flowering perennial shrub, upright and slightly outward branching.

Overall plant shape: Upright.

Height: Approximately 52 cm.

Plant spread: Approximately 64 cm.

Plant vigor: Strong, persistent.

Branching characteristics: Upright and outward, basal branches, some pinching required.

Length of lateral branches: Approximately 45 cm.

Number of lateral branches: Approximately 12.

Diameter of lateral branches: 1.5 cm.

Lateral branch shape and appearance: Rounded and slightly woody.

Lateral branch strength: Strong, rigid.

Internode length: 4.3 cm.

Branch color: Immature: Near RHS White 155B with striations of Greyed-purple 186B. As it develops, turns to a darker Greyed-purple 187D. Mature: Near RHS Grey-brown 199B blended with Greyed-purple 187D.

Branch aspect: 0-35° from center of plant.

Branch pubescence: Yes.

FOLIAGE

Leaf:

- *Arrangement*.—Opposite.
- *Average length*.—New: 1.2 cm, Mature: 5.8 cm.
- *Average width*.—New: 0.7 cm, Mature: 4.8 cm.
- *Shape of blade*.—Ovate.
- *Apex*.—Acute.
- *Base*.—Rounded.
- *Margin*.—Serrulate.
- *Texture and appearance of top surface*.—Smooth, coriaceous.
- *Texture and appearance of bottom surface*.—Slightly pubescent, rugose.
- *Leaf pubescence*.—Slightly on both sides.
- *Color*.—Young foliage upper side: Near RHS Green 143A fading to Yellow-green 145A at the base. Young foliage under side: Near RHS Green 141D. Mature foliage upper side: Near RHS Green 143A. Mature foliage under side: Near RHS Green 139C.
- *Venation*.—Type: Pinnate. Venation color upper side: Near RHS Yellow-green 148A. Venation color under side: Near Yellow-Green 145D.

Petiole:

- *Average length*.—New: 3 mm, Mature: 7 mm.
- *Diameter*.—1.5 cm.
- *Color*.—Upper side: Near RHS Red-purple 59B with Yellow-green 145A at the very base. Under side: Near RHS Yellow-green 145B with a slight striation of Red-purple 59C along the sides.
- *Texture upper side*.—Smooth, coriaceous.
- *Texture under side*.—Smooth, coriaceous, slightly pubescent.

FLOWER

Bloom period:

- *Natural season*.—Early Summer through Fall.

Inflorescence:

- *Type*.—Mophead.
- *Quantity of flowers per inflorescence*.—Fertile flowers, 34 approximately. Sterile Flowers, 440 approximately.
- *Persistent or self-cleaning*.—Persistent.
- *Fragrance*.—Slightly sweet.

Panicle:

- *Shape*.—Cone.
- *Height*.—15 cm.
- *Diameter*.—14 cm.

Sterile flower:

- *Androecium*.—Yes.
- *Bud shape*.—Orbicular.
- *Bud length*.—2 mm.
- *Bud diameter*.—2.5 mm.
- *Bud color*.—Near RHS Whited 155B with Red-purple 63C on top.
- *Flower aspect*.—Upright.
- *Flower shape*.—Crucifix.
- *Flower length*.—2 cm.
- *Flower diameter*.—5 cm.
- *Flower depth*.—5 cm.

Sterile flower petals:

- *Length of petal*.—2 mm.
- *Width of petal*.—1 mm.
- *Apex*.—Acute.
- *Shape of petal*.—Ovate.
- *Petal margin*.—Entire.
- *Petal arrangement*.—Whorled.
- *Petal base*.—Rounded to obtuse.
- *Petal number*.—4.
- *Petal texture*.—Smooth, coriaceous, upper and under side.

*Color*.—Upper surface at first opening: Near RHS White 155B. Upper surface at maturity: Near RHS White 155B. Under surface at first opening: Near RHS White 155B. Under surface at maturity: Near RHS White 155B.

Sterile flower sepal:
*Arrangement*.—Whorl.
*Number*.—4-5.
*Shape*.—Ovate.
*Tip*.—Acute.
*Base*.—Obtuse.
*Margin*.—Entire.
*Length*.—2 cm.
*Width*.—2.4 cm.
*Texture, upper*.—Smooth, coriaceous.
*Texture, lower*.—Smooth, coriaceous.
*Color*.—Upper surface at first opening: Near RHS White 155B. Upper surface at maturity: Near RHS White 155B with light speckling/blending with Red-purple 63C. Under surface at first opening: Near RHS White 155B. Under surface at maturity: White 155B with light speckling/blending with Red-purple 63C. Upper surface fading to: Near RHS Greyed-purple 184A. Under surface fading to: Near RHS Greyed-purple 184A.

Sterile flower pedicel:
*Length*.—1.5 cm.
*Diameter*.—1 mm.
*Angle*.—Upright and outward.
*Strength*.—Good.
*Texture*.—Smooth.
*Color*.—Near RHS White 155B.

Fertile flower:
*Bud shape*.—Orbicular.
*Bud length*.—3 mm.
*Bud diameter*.—3 mm.
*Bud color*.—Near RHS Red-purple 68D.
*Flower aspect*.—Upright.
*Flower shape*.—Star-like.
*Flower length*.—5 mm.
*Flower diameter*.—5 mm.
*Flower depth*.—3 mm.

Fertile flower petals:
*Length of petal*.—2.5 mm.
*Width of petal*.—1 mm.
*Apex*.—Acute.
*Shape of petal*.—Ovate.
*Petal margin*.—Entire.
*Petal arrangement*.—Whorl.
*Petal number*.—5.
*Petal base*.—Rounded.
*Petal texture*.—Smooth, upper and under side.
*Color*.—Upper surface at first opening: Near RHS White 155B. Upper surface at maturity: Near RHS White 155B with Red-purple 63B on the tips and along the edges. Under surface at first opening: Near RHS White 155B. Under surface at maturity: Near RHS White 155B with Red-purple 63B on the tips and along the edges. Upper surface fading to: Near RHS White 155B with Red-purple 63B on the tips and along the edges. Under surface fading to: Near RHS White 155B with Red-purple 63B on the tips and along the edges.

Fertile flower pedicel:
*Angle*.—Outward/upright.
*Strength*.—Good.
*Length*.—2 mm.
*Width*.—0.5 mm.
*Texture*.—Smooth.
*Color*.—Near RHS White 155B.

Fertile flower sepal:
*Arrangement*.—Whorl.
*Number*.—5.
*Shape*.—Ovate.
*Tip*.—Acute.
*Base*.—Fused.
*Margin*.—Entire.
*Length*.—1 mm.
*Width*.—1 mm.
*Texture, upper*.—Smooth.
*Texture, lower*.—Smooth.
*Color*.—Upper surface at first opening: Near RHS Yellow 8D. Upper surface at maturity: Near RHS Yellow 8D. Under surface at first opening: Near RHS Yellow 8D. Under surface at maturity: Near RHS Yellow 8D. Upper surface fading to: Near RHS Yellow 8D. Under surface fading to: Near RHS Yellow 8D.

REPRODUCTIVE ORGANS

Sterile flower:
*Stamen number*.—8.
*Filament length*.—0.7 mm.
*Filament color*.—Near RHS White 155B.
*Anther shape*.—Rounded, fusiform.
*Anther color*.—Near RHS Greyed-yellow 162D.
*Anther length*.—1 mm.
*Pollen amount*.—Very little.
*Pollen color*.—Near RHS Greyed-yellow 163D.
*Gynoecium*.—No.

Fertile flower:
*Stamen number*.—10.
*Filament length*.—3 mm.
*Filament color*.—Near RHS White 155B.
*Anther shape*.—Oblong.
*Anther length*.—1 mm.
*Anther color*.—Near RHS Greyed-yellow 160B.
*Pollen amount*.—Some.
*Pollen color*.—Near RHS Greyed-yellow 160B.
*Pistil number*.—1, two-lobed.
*Pistil length*.—2.5 mm.
*Stigma shape*.—Club.
*Stigma color*.—Near RHS Greyed-yellow 160C.
*Style length*.—1 mm.
*Style color*.—Near RHS Greyed-yellow 160C.
*Ovary color*.—Near RHS Yellow-green 150B.

OTHER CHARACTERISTICS

Disease resistance: Neither resistance nor susceptibility to diseases or pests has been observed in this variety.
Cold tolerance: −31° C. to 38° C.
Fruit/seed production: No fruits/seeds detected to date.
Other traits: Good strong branches.

What is claimed is:

1. A new and distinct cultivar of *Hydrangea* plant named 'SMHPCW' as herein illustrated and described.

* * * * *